United States Patent [19]
McTeigue et al.

[11] Patent Number: 6,149,943
[45] Date of Patent: Nov. 21, 2000

[54] MICROCRYSTALLINE CELLULOSE PARTICLES HAVING ACTIVE CORE

[75] Inventors: Daniel McTeigue; Indukumar G. Shah, both of North Wales; Karen Swider, W. Conshohocken; David W. Wynn, Abington, all of Pa.

[73] Assignee: McNeil-PPC, Inc., Skillman, N.J.

[21] Appl. No.: 09/431,899

[22] Filed: Nov. 2, 1999

Related U.S. Application Data

[62] Division of application No. 09/148,251, Sep. 4, 1998, Pat. No. 5,997,905.

[51] Int. Cl.$^7$ ............... A61K 9/16; A61K 9/20; A61K 9/22; A61K 9/26
[52] U.S. Cl. ............ 424/494; 424/464; 424/468; 424/469; 424/497
[58] Field of Search .................. 424/490, 494, 424/493, 489, 479

[56] References Cited

U.S. PATENT DOCUMENTS

| | | | |
|---|---|---|---|
| 4,851,226 | 7/1989 | Julian et al. | 424/441 |
| 5,077,051 | 12/1991 | Gallopo et al. | 424/435 |
| 5,112,621 | 5/1992 | Stevens et al. | 424/497 |
| 5,356,896 | 10/1994 | Kabadi et al. | 514/256 |
| 5,384,130 | 1/1995 | Kamada | 424/461 |
| 5,427,800 | 6/1995 | Cingotti | 424/489 |
| 5,429,825 | 7/1995 | Reo et al. | 424/490 |
| 5,489,436 | 2/1996 | Hoy et al. | 424/441 |
| 5,505,983 | 4/1996 | Kamada | 427/2.21 |
| 5,529,783 | 6/1996 | Burke et al. | 424/441 |
| 5,547,948 | 8/1996 | Barcomb | 514/170 |
| 5,780,055 | 7/1998 | Habib et al. | 424/464 |
| 5,997,905 | 7/1998 | McTeigue et al. | 424/490 |

FOREIGN PATENT DOCUMENTS

| | | |
|---|---|---|
| 289733 | 11/1996 | Taiwan . |
| 94/09762 | 11/1994 | WIPO . |

OTHER PUBLICATIONS

Avicel PH Microcrystalline Cellulose, NJ, Ph.Eur., JP, BP, FMC Corp., Aug. 3, 1998.
Avicel PH Microcrystalline Cellulose, NJ, Ph.Eur., JP, BP,; Focut on Differentiated Prod. FMC Corp., 1994.
Celphere Microcrystalline Cellulose Spheres, FMC orp., Oct. 1995.

*Primary Examiner*—Thurman K. Page
*Assistant Examiner*—Susan Tran

[57] ABSTRACT

The present invention provides a core of predominately microcrystalline cellulose, on which an active drug is layered onto the core via solution coating. The coated particles have a narrower particle size distribution than coated granules provided by other processes. An optional final coating of a pharmaceutically acceptable polymeric coating is provided to provide tastemaking or controlled release, and protection of the drug-layered particles.

9 Claims, 3 Drawing Sheets

500 μm

500 μm

500 μm

500 μm

500 μm 6,149,943

MICROCRYSTALLINE CELLULOSE PARTICLES HAVING ACTIVE CORE

RELATED APPLICATIONS

This application is a divisional application of U.S. Ser. No. 09/148,251, filed on Sep. 4, 1998 is now U.S. Pat. No. 5,997,905, the contents of which are hereby incorporated by reference as if set forth in its entirety.

FIELD OF THE INVENTION

This invention relates to the solution layering of pharmaceutically active drug on a predominately microcrystalline cellulose core.

BACKGROUND OF THE INVENTION

It is well known in the pharmaceutical art to apply a pharmaceutically active material to a smooth, spherical core. Typically, the process involves the application of a solution, suspension, or powder coating of the spherical core with the pharmaceutically active ingredient.

For example, Jones, D. M., in the chapter entitled, Solution and Suspension Layering, *Pharmaceutical Pelletization Technology*, describes layering a solution of drug onto seed material, generally a coarse crystal or nonpareil, in coating pans or fluidized bed equipment. The chapter notes that the Wurster process can be used for coating and layering onto substrates as small as 100 microns, and coated layers of 100 to 150% of the starting batch weight may be applied. The author also notes that a binder is optional, but recommended, when applying drug from a solution.

Despite the teachings of the prior art, it is highly desirable to apply a pharmaceutically active material via solution coating that does not require a separate granulation step in order to increase the size of the substrate core prior to coating.

SUMMARY OF THE INVENTION

The present invention is directed to a particle which comprises a seed core comprised predominately of microcrystalline cellulose, having an average particle size of about 180 microns, to which a pharmaceutically active ingredient in solution is layered onto the microcrystalline cellulose by spray coating. The seed core and the pharmaceutically active material is then overcoated with a suitable polymer. The mean particle diameter of the final coated particle containing the pharmaceutically active ingredient and polymer is less than about 325 microns, which makes it smaller than traditional particles.

More specifically the present invention comprises a particle comprising a center core of predominately microcrystalline cellulose having an average particle size of about 160 to about 220 microns with a particle size standard deviation of from about 75 to about 200;

pharmaceutically active material coating the center core of microcrystalline cellulose;
wherein the coated particle is from about 40 to about 75 weight percent microcrystalline cellulose;
pharmaceutically active ingredient is from about 25 to about 60 weight percent; and a particle size of from about 200 to about 325 microns and a particle size standard deviation of from about 30 to about 175 microns.

The present invention also includes a method for making a pharmaceutically active particle comprising providing a center core of predominately microcrystalline cellulose having an average particle size of about 160 to about 220 microns with a particle size standard deviation of from about 75 to about 200;
coating said microcrystalline cellulose with a pharmaceutically active ingredient;
wherein the coated particle is from about 40 to about 75 weight percent microcrystalline cellulose; the pharmaceutically active ingredient is from about 25 to about 60 weight percent; and has a particle size of from about 200 to about 325 microns and a particle size standard deviation of from about 30 to about 175 microns; wherein the coating of the microcrystalline cellulose is performed in the absence of a granulation step.

DETAILED DESCRIPTION

The seed core of the present invention is predominately microcrystalline cellulose. By predominately, it is understood that the seed core is greater than 90 weight percent, preferably greater than 95 weight percent and in a most preferred embodiment the seed core is entirely microcrystalline cellulose. Microcrystalline cellulose is uniquely well-suited as a substrate for film coating due to its surface characteristics, the abundance of free hydroxyl groups which improve film adhesion, and its insolubility which aids in processing. The preferred source of microcrystalline cellulose is Avicel PH 200 available from FMC Corp. The preferred microcrystalline cellulose has a rough porous surface, a non-spherical shape, a median particle diameter of about 160 to about 220 microns and a narrow particle size distribution (standard deviation from about 75 to about 200 microns), with more than 50%, and preferably more than 60 percent of the particles between about 177 and about 300 microns. Avicel PH200 has a nominal particle size of about 180 microns with a low proportion of fines, less than 25% by weight of particles smaller than 125 microns.

In addition the microcrystalline cellulose should have a tapped bulk density of from about 0.40 to about 0.45 grams/cubic centimeters.

Figure 1:
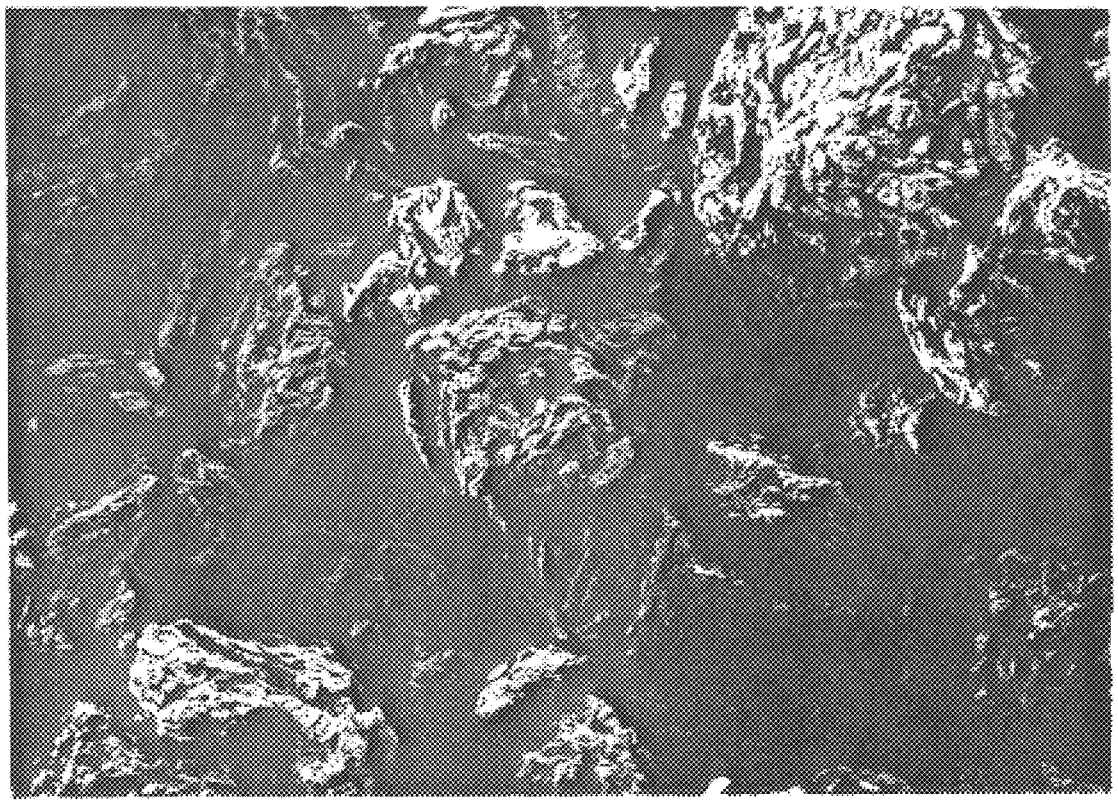
FIG. 1 is a photomicrograph of the preferred microcrystalline cellulose.
Figure 2:
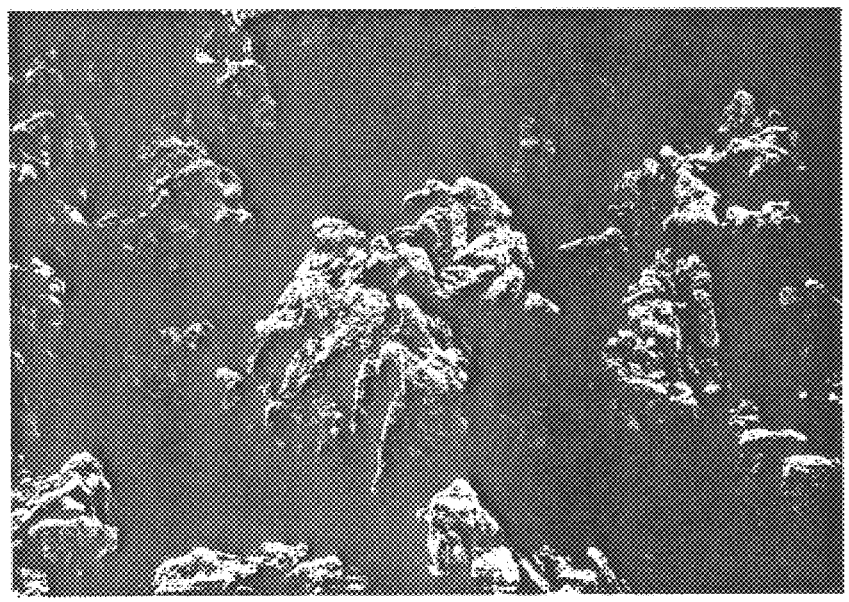
FIG. 2 is a photomicrograph of the microcrystalline cellulose depicted in FIG. 1 layered with a pharmaceutically active ingredient.
Figure 4A:
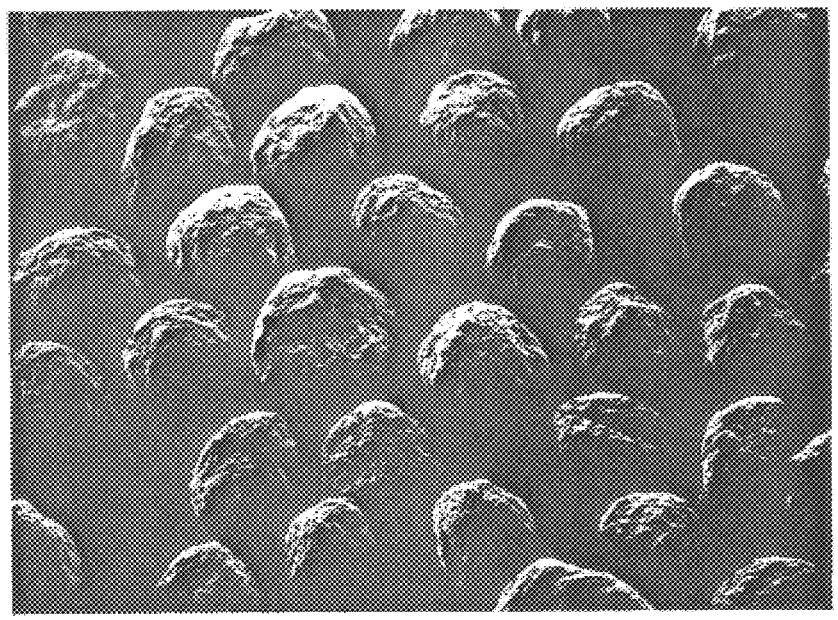
FIG. 4a and FIG. 4b are photomicrographs of commercially available microcrystalline cellulose materials.
Figure 4B:
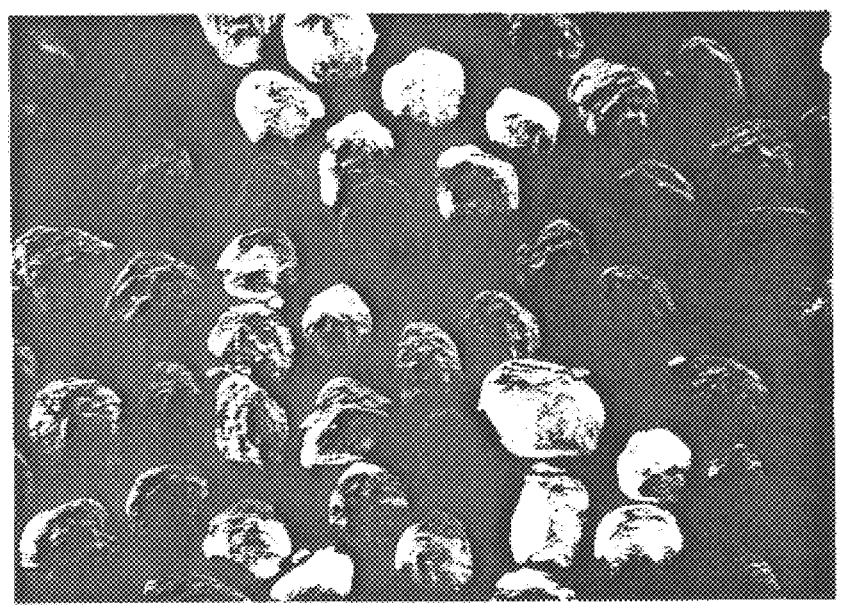

Another key characteristic of the preferred microcrystalline cellulose is the irregular shape of the surface of the microcrystalline cellulose. The microcrystalline cellulose is preferably irregular in surface characteristics, see FIG. 1. The irregular surface morphology provides porosity and allows the pharmaceutically active ingredient to be applied to the surface and to be adhered or retained on the surface, see FIG. 2, pseudoephedrine hydrochloride, dextromethorphan hydrobromide, and chlorpheniramine maleate layered on the microcrystalline cellulose surface, see Example 1 below. Surprisingly we have found that the irregular surface morphology of the preferred microcrystalline cellulose provides a better surface to layer the pharmaceutically active material than other microcrystalline cellulose products sold for this purpose, which have a more smooth surface and higher degree of sphericity see FIGS. 4a and 4b, Celphere 203 and 102(FMC Corp.), depicted in FIGS. 4a and 4b respectively.

Greater surface porosity on the microcrystalline cellulose allows the pharmaceutically active material to be layered or adsorbed with minimal effect on flowability. Better flow leads to superior blend homogeneity and tablet content uniformity, which are critical quality aspects of the process and product. Commercially available products such as Celphere 203 and 102(FMC Corp.), are regular, spherical particles, having aspect ratios of about 1, which also lack the desired surface characteristics.

Until now it has been widely believed that smooth spherical particles were the best substrates for coating. U.S. Pat. Nos. 5,384,130, 5,505,983, the contents of both patents hereby incorporated by reference, disclose the disadvantages of using sugar spheres, especially for aqueous layering processes, since they dissolve readily in water leading to agglomeration, and provide a more highly friable coated particle subject to fracture. Fracture of the particle coating compromises it's functionality, whether it is used for the purpose of controlled release, or tastemasking. Generally, substrates used for particle coating are prepared by rotor-granulation or other agglomeration processes to achieve. a average particle size of at least about 250 microns. The size of substrate which may be successfully coated without unwanted agglomeration of particles has previously been limited by the size of droplets which may be obtained from the available atomizing spray guns. Improvements in spray gun technology have lead to smaller droplet sizes, allowing for the successful coating of smaller substrates.

Another benefit of the preferred microcrystalline cellulose is the narrow particle size distribution associated with the microcrystalline cellulose and the particles which contain the pharmaceutically active material. The particle size standard deviation is a term that is understood in the art, see Lachman L., Lieberman H., *Pharmaceutical Dosage Forms: Tablets* (V2), Dekker Inc, New York, 1981, pages 185–202, and is a measure of the homogeneity of the particles with respect to particle size. The present invention employs microcrystalline celluloses with a particle size standard deviation of from about 75 to about 200 microns, preferably from about 80 to about 150; and most preferably from about 85 to about 95 microns.

Solution layering of the pharmaceutically active material requires that the pharmaceutically active material is first dissolved in a solvent and is then sprayed onto the surface of the microcrystalline cellulose. Preferably the solvent is water, however other pharmaceutically acceptable solvents may also be employed including, but not limited to, methanol acetone and mixtures thereof. The selection of solvent is based upon the pharmaceutically active material that is to be layered onto the core particle.

The pharmaceutically active material to be applied to the microcrystalline cellulose core is not critical as long as it is dissolved in the solvent. The use of pharmaceutically active materials provided within a suspension or a dispersion are also provided within the scope of the invention provided that pharmaceutically acceptable suspending or emulsifying agents are employed. The pharmaceutically active ingredient must be soluble in an acceptable solvent so that it can be applied to the core particle. Suitable active ingredients include pharmaceuticals, minerals, vitamins and other nutraceuticals. Suitable pharmacuticals include but are not limited to analgesics, decongestants, expectorants, antitussives, antihistamines, gastrointestinal agents, diuretics, bronchodilators, sleep-inducing agents and mixtures thereof. Preferred pharmaceutical active ingredients for solution layering include pseudoephedrine, phenylpropanolamine, chlorpheniramine, dextromethorphan, diphenhydramine, doxylamine, loperamide, mixtures thereof and pharmaceutically acceptable salts thereof. Preferred pharmaceutical active ingredients for suspension layering include acetaminophen, ibuprofen, flurbiprofen, naproxen, aspirin, famotidine, loperamide, ranitidine, cimetidine, astemizole, terfenadine, terfenadine carboxylate, loratadine, cetirizine, mixtures thereof and pharmaceutically acceptable salts thereof.

The weight percent of the pharmaceutically active ingredient in the solution is typically in the range of from about 5 to 75, preferably from about 40 to about 60 and most preferably about 45 to about 56 weight percent in the solution. The solution is sprayed onto the surface of the microcrystalline cellulose, preferably by the use of rotor or Wurster coating. These processes as well as other suitable methods are known in the art.

The amount of drug active to be layered onto the substrate particles is determined by the desired dose in the finished product.

Figure 3:
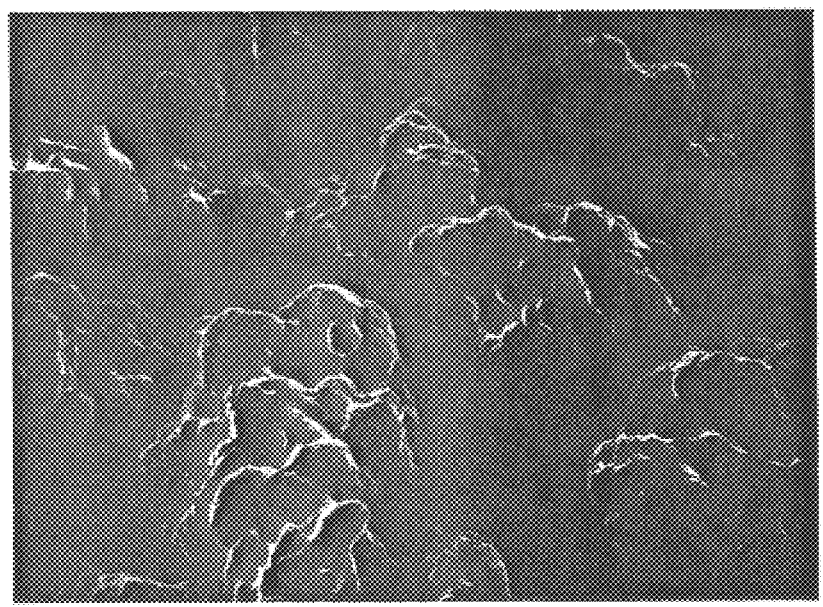
FIG. 3 is a photomicrograph of the particles of the invention with a polymer coating.

If the active ingredient has an objectionable taste, or if controlled release is desired, the particle containing the active ingredient may be coated with a polymer system, 70/30 mixture of cellulose acetate and EUDRAGIT E 100 (see FIG. 3). The active may be coated with coatings known in the art, such as those described in U.S. Pat. Nos. 4,851, 226, 5,075,114, 5,489,436, all of which are hereby incorporated by reference. The coating may provide for immediate or sustained release of the active.

Suitable coating compositions, include but are not limited to the coatings provided in the following table:

| Polymer System | Coat Level[1] | Polymer Ratio[2] |
|---|---|---|
| Cellulose Acetate/PVP | 5–60% | 90/10 to 60/40 |
| Cellulose Acetate Butyrate/PVP | 5–60% | 90/10 to 60/40 |
| Cellulose Acetate/HPC | 5–60% | 90/10 to 50/50 |
| Cellulose Acetate Butyrate/HPC | 5–60% | 90/10 to 50/50 |
| Cellulose Acetate/ EUDRAGIT E100 | 8–60% | All ratios |
| Cellulose Acetate Butyrate/ EUDRAGIT E 100 | 8–60% | All ratios |
| Ethyl Cellulose/PVP | 8–60% | 90/10 to 60/40 |
| Ethyl Cellulose/HPC | 8–60% | 90/10 to 50/50 |
| Ethyl Cellulose/EUDRAGIT E 100 | 8–60% | All ratios |
| HPC | 10–60% | NA |
| HEC | 10–60% | NA |
| EUDRAGIT E 100 | 10–60% | NA |
| HPMC | 10–60% | NA |
| HEC/HPMC | 10–60% | All ratios |
| HPC/HPMC | 10–60% | All ratios |
| HEC/HPC | 10–60% | All ratios |
| 2-vinyl pyrridine styrene co-polymer | 10–60% | NA |
| CA/2-vps | 8–60% | All ratios |
| CAB/2-vps | 8–60% | All ratios |
| Ethyl Cellulose/2-vps | 8–60% | All ratios |
| Cellulose Triacetate/PVP | 8–60% | 90/10 to 60/40 |

| Polymer System | Coat Level[1] | Polymer Ratio[2] |
| --- | --- | --- |
| Cellulose Triacetate/HPC | 8–60% | 90/10 to 50/50 |
| Cellulose Triacetate/ EUDRAGIT E 100 | 8–60% | All ratios |

[1]Percent by weight of the coated particle in a dried state.
[2]By weight.
PVP, polyvinylpyrrolidone; HPC Hydroxypropyl cellulose HEC - Hydroxyethyl cellulose; HPMC - Hydroxypropylmethyl cellulose; CA - Cellulose Acetate CAB - Cellulose Acetate Butyrate 2-VPS - 2-Vinyl pyridine styrene EUDRAGIT ™ E-100 - methylaminoethyl-methacrylate and neutral methacrylic acid esters available from Rohm Pharma GmbH, Germany.

The final particle comprises an inactive core particle, the pharmaceutically active drug layered onto the core and the optional polymer coating. The drug active loaded on to the microcrystalline cellulose is typically present at a level of from about 10 to about 75 weight percent, preferably from about 25 to about 60 weight percent and most preferably from about 30 to about 50 weight percent of the weight of the final drug-layered coated particle.

The present invention is an improvement over the prior art in that the particle size distribution of the coated particles is narrower than the particles previously made. The narrower distribution of particle size is a result of the preferred starting material and the absence of an agglomeration step to form the core prior to drug layering onto the particles. The prior art discloses the granulation or agglomeration of the inactive core particles which are then layered with drug and coated. This results in a wider distribution of particle size, which provides a gritty texture in the mouth. The present invention provides a smaller particle with a narrower distribution of particle size, which results in a less gritty texture/mouthfeel.

The drug layered particle size distribution is narrower than for other processes, said standard deviation ranging from about 30 to about 175 microns, more preferably from about 65 to about 120, and most preferably from about 75 to about 100 microns.

Because the final particles are also smaller than those previous disclosed, and there is a polymeric coating covering the pharmaceutically active materials, the particles have a plastic coating which is difficult to fracture. This coating provides a pleasant taste which makes them particularly well suited for a chewable tablet.

A further advantage is the elimination of the granulation step in the manufacturing method. These benefits are accomplished without the agglomeration and flow problems previously encountered. A further advantage is because the granulation step is avoided, the size distribution of the particles is more narrow than with traditional methods. This provides improved flow characteristics as well as avoiding fines which cause unwanted agglomeration during the process or plugging of process equipment. Narrow size distribution of the substrate for drug layering or further polymer coating is also a processing advantage, reducing agglomeration due to sticking of small particles to larger particles.

A further advantage of the present invention is the flexibility of the process. The present invention can be used to apply coatings which can include extended release, time release, enteric coatings and the like.

In addition to the microcrystalline cellulose in the core, additional excipients can be added to the core, including but not limited to lactose, starches, mannitol and the like. Typically the excipients are less than about 10 percent by weight of the final product. The inclusion of these excipients is not preferred since they tend to increase the particle size distribution of the coated product.

After the coated particles are formed, the particles are then combined with excipients well known in the art, and compressed to provide a capsule or tablet.

The following examples are provided to further illustrate the claimed invention, but not limit the invention to the examples provided below. Unless noted to the contrary, all parts are parts by weight.

EXAMPLE 1

Drug-layered Particles

This example provides a formulation and process for making a drug-coated particle which is suitable for use as a substrate for further particle coating with any of a number of polymers or polymer combinations. In this example, the particle contains three active ingredients. Single active ingredient particles may be prepared by a similar method. Unless otherwise noted, all parts are understood to be parts by weight.

An aqueous solution was prepared, containing the following ingredients (total weight 3.03 kg):

| | |
| --- | --- |
| Pseudoephedrine Hydrochloride | 15 parts |
| Dextromethorphan Hydrobromide | 5 parts |
| Chlorpheniramine Maleate | 1 part |
| Polyvinyl Pyrrolidone (K29/32) | 2.27 parts |
| Purified Water | 22.8 parts |

Microcrystalline cellulose (Avicel 200, 3.47 kg) was charged into a fluidized bed coating apparatus (Glatt Model GPCG 5/9). The microcrystalline cellulose was then fluidized by a flow of air at an inlet temperature of 46° C. The drug-containing layering solution was then sprayed onto the fluidized microcrystalline cellulose particles at a rate of 65 grams/min. until coated microcrystalline cellulose particles containing approximately 31% by weight of the drug-containing coating were obtained.
Particle Size Distribution of microcrystalline cellulose starting material(based on normal distribution model): Median: 213 microns, Standard deviation: 191 microns
Size distribution of drug-layered particles (based on normal distribution model): Median: 293 microns, Standard deviation: 160 microns
Assay Results
The drug-layered particles in this example were found to have drug potencies of 23.6% pseudoephedrine hydrochloride, 6.72% dextromethorphan hydrobromide, and 1.36% chlorpheniramine maleate.

EXAMPLE 2

Pseudoephedrine Layered Avicel PH200 with PVP

This example provides a formulation and process for making a drug-coated particle which is suitable for use as a substrate for further particle coating with any of a number of polymers or polymer combinations. In this example, the particle contains pseudoephedrine hydrochloride as the active ingredient, with polyvinyl pyrrolidone as the binder.

An aqueous solution was prepared, containing the following ingredients (total weight 3.62 kg):

| | |
|---|---|
| Pseudoephedrine Hydrochloride | 55.3% |
| Polyvinyl Pyrrolidone (K29/32) | 1.1% |
| Purified Water | 43.6% |

Microcrystalline cellulose (Avicel 200, 1.96 kg) was charged into a Rotor (tangential spray) fluidized bed coating apparatus (Glatt Model GPCG 5/9). The microcrystalline cellulose was then fluidized by a flow of air at an inlet temperature of 36° C. The drug-containing layering solution was then sprayed onto the fluidized microcrystalline cellulose particles at a rate of 80 grams/min. until coated microcrystalline cellulose particles containing approximately 50% by weight of the drug-containing coating were obtained.

Size distribution of drug-layered particles: (based on normal distribution model): Median: 238 microns, Standard deviation: 77 microns

EXAMPLE 3

Tastemasked Coated Drug-layered Particles

This example provides a formulation and process for further coating the drug layered particles in example 2 with polymer for tastemasking. In this example, the tastemasking polymer system was a combination of cellulose acetate and Eudragit E-100. Tastemasked coated particles may be prepared by a similar method, using other polymer systems.

A solution was prepared, containing Cellulose Acetate 398-10 (Eastman Chemical) and Eudragit E-100 (Rohm Pharma) at a level of 12% solids in acetone (total weight 10.7 kg). The ratio of cellulose acetate to Eudragit E-100 was 95:5.

A portion (3.0 kg) of the drug layered particles produced in Example 2 was charged into a rotor (tangential spray) fluidized bed coating apparatus (Glatt Model GPCG 5/9). The drug-layered particles were then fluidized by a flow of air at an inlet temperature of 36° C. The polymer coating solution was then sprayed onto the fluidized particles at a rate of 40 grams/min. until coated drug particles containing approximately 30% by weight of the polymer coating were obtained.

Size distribution of polymer-coated, drug-layered particles (based on normal distribution model): Median: 283 microns, Standard deviation: 84 microns

EXAMPLE 4

Diphenhydramine Layered Avicel PH200 (no binder used)

This example provides a formulation and process for making a drug-coated particle which is suitable for use as a substrate for further particle coating with any of a number of polymers or polymer combinations. In this example, the particle contains diphenhydramine as the active ingredient, with no added binder.

An aqueous solution was prepared, containing the following ingredients (total weight 3.58 kg):

| | |
|---|---|
| Diphenhydramine | 56% |
| Purified Water | 44% |

Microcrystalline cellulose (Avicel 200, 2.0 kg) was charged into a Rotor (tangential spray) fluidized bed coating apparatus (Glatt Model GPCG 5/9). The microcrystalline cellulose was then fluidized by a flow of air at an inlet temperature of 38° C. The drug-containing layering solution was then sprayed onto the fluidized microcrystalline cellulose particles at a rate of 30 grams/minutes until coated microcrystalline cellulose particles containing approximately 50% by weight of the drug-containing coating were obtained.

Size distribution of drug-layered particles: (based on normal distribution model): Median: 302 microns, Standard deviation: 94 microns Flow analysis demonstrated this material remained free-flowing after 4 days at 40° C./75% RH. (open dish)

EXAMPLE 5

Tastemasked Coated Drug-layered Particles

This example provides a formulation and process for further coating the drug layered particles in example 4 with polymer for tastemasking. In this example, the tastemasking polymer system is a combination of cellulose acetate and Eudragit E-100. Tastemasked coated particles may be prepared by a similar method, using other polymer systems.

A solution was prepared, containing Cellulose Acetate 398-10 and Eudragit E-100 at a level of 12% solids in Acetone (total weight 10.7 kg). The ratio of cellulose acetate to Eudragit E-100 was 95:5.

A portion (3.0 kg) of the drug layered particles produced in example 2 was charged into a Rotor (tangential spray) fluidized bed coating apparatus (Glatt Model GPCG 5/9). The drug-layered particles were then fluidized by a flow of air at an inlet temperature of 36° C. The polymer coating solution was then sprayed onto the fluidized particles at a rate of 35 grams/min. until coated drug particles containing approximately 30% by weight of the polymer coating were obtained.

Size distribution of Polymer-coated. drug-layered particles (based on normal distribution model): Median: 309 microns, Standard deviation: 91 microns

EXAMPLE 6

Chewable Tablets

Tastemasked coated diphenhydramine particles, and tastemasked coated pseudoephedrine hydrochloride particles, prepared in the manner described above, were combined with tastemasked acetaminophen particles (prepared according to methods disclosed in U.S. Pat. No. 4,851,226) and the following inactive ingredients to produce chewable tablets, using the process described below:

| Material | Quantity (mg/tablet) |
| --- | --- |
| CA/PVP Coated Acetaminophen (89% potent) | 90.91 |
| CA/E100 Coated Pseudoephedrine Hydrochloride (35% potent) | 21.43 |
| CA/E100 Coated Diphenhydramine Hydrochloride (35% potent) | 17.86 |
| Mannitol USP (Granular) | 284.56 |
| Microcrystalline Cellulose NF | 36.0 |
| Aspartame NF | 9.6 |
| Flavor | 14.6 |
| Color (lakes) | 0.24 |
| Magnesium Stearate NF | 4.8 |
| Tablet Weight | 480 | a. All ingredients except magnesium stearate were combined in a PK blender, and blended for 25 minutes. The magnesium stearate was to the blender and blending was continued for an additional 5 minutes.

b. Tablets were compressed to the following specifications on a Manesty Betapress using 13/32-inch diameter, round flat-faced beveled edge tooling:

|  | Target |
| --- | --- |
| Weight (mg: average of 10) | 480 |
| Thickness (mm: average of 5) | 4.8 |
| Hardness (kp: average of 5) | 6.0 |
| Friability (% loss: 20 tablets) | <1.0 |

Resulting tablets had good taste characteristics with minimal bitterness.

COMPARATIVE EXAMPLE 1

Celphere 203

This example provides a formulation and process for layering diphenhydramine onto Celphere 203 (FMC Corp.) a commercially available product marketed as an ideal substrate for drug-layering and particle coating.

A.) An aqueous solution was prepared, containing the following ingredients (total weight 2.68 kg):

| Diphenhydramine | 56% |
| --- | --- |
| Purified Water | 44% |

Microcrystalline cellulose (Celphere 203, 1.5 kg) was charged into a Rotor (tangential spray) fluidized bed coating apparatus (Glatt Model GPCG 5/9). The Microcrystalline cellulose was then fluidized by a flow of air at an inlet temperature of 34° C. The drug-containing layering solution was then sprayed onto the fluidized Microcrystalline cellulose particles at a rate of 20 grams/min. until coated Microcrystalline cellulose particles containing approximately 50% by weight of the drug-containing coating were obtained.

Flow analysis demonstrated this material became sticky and not free-flowing after 4 days at 40° C./75% Relative Humidity. (open dish)

B.) The drug layered particles were further coated with polymer for tastemasking. In this example, the tastemasking polymer system is a combination of cellulose acetate and Eudragit E-100. A solution was prepared, containing Cellulose Acetate 398-10 and Eudragit E-100 at a level of 12% solids in Acetone (total weight 3.3 kg). The ratio of cellulose acetate to Eudragit E-100 was 70:30.

A portion (1.0 kg) of the drug layered particles produced in part A was charged into a Rotor (tangential spray) fluidized bed coating apparatus (Glatt Model GPCG 5/9). The drug-layered particles were then fluidized by a flow of air at an inlet temperature of 32° C. The polymer coating solution was then sprayed onto the fluidized particles at a rate of 20 grams/min. until coated drug particles containing approximately 30% by weight of the polymer coating were obtained.

Size distribution of drug-layered particles: (based on normal distribution model): Median: 373 microns, Standard deviation: 84 microns Size distribution of polymer-coated, drug-layered particles (based on normal distribution model): Median: 399 microns, Standard deviation: 83 microns

COMPARATIVE EXAMPLE 2

Lactose granules with Methocel E5 (Dow) binder were used as a substrate for layering pseudoephedrine hydrochloride and dextromethorphan hydrobormide, then coating with CA:E100 at a 60% level. Resulting tablets were gritty (due to large particle size) and slow to dissolve (due to 60% coating level).

COMPARATIVE EXAMPLE 3

Avicel PH101 (FMC Corp.) was rotor granulated together with pseudoephedrine hydrochloride, dextromethorphan hydrobromide, and chlorpheniramine maleate. Resulting product had median diameter of 51 microns with standard deviation of 270 microns. A high degree of agglomeration and a high degree of fine particles were observed visually.

COMPARATIVE EXAMPLE 4

Direct coating of the individual (psedoephedrine and diphenhydramine) active particles was attempted, but not pursued further due to excessive agglomeration and poor tastemasking.

COMPARATIVE EXAMPLE 5

Granulating amines (pseudoephedrine and diphenhydramine) together with powdered acetaminophen using water or hydroxypropyl methyl cellulose binder solution was attempted, but not pursued due to a eutectic mixture formation between diphenhydramine and the other ingredients. Moisture adsorption studies suggested that pseudoephedrine and diphenhydramine undergo a solid state interaction at relative humidities >75% resulting in formation of a deliquescent material.

I claim:

1. A particle comprising:
    a center core of greater than about 90 weight percent microcrystalline cellulose having an average particle size of about 160 to about 220 microns with a particle size standard deviation of from about 75 to about 200 microns;
    pharmaceutically active material coating the center core of microcrystalline cellulose and a tapped bulk density of from about 0.40 to about 0.45 grams per cubic centimeters;
    wherein the coated particle is from about 40 to about 75 weight percent microcrystalline cellulose; pharmaceutically active ingredient is from about 25 to about 60 weight percent; and a particle size of from about 200 to about 325 microns and a particle size standard deviation of from about 30 to about 175 microns.

2. The particle of the claim 1 wherein the center core is greater than about 95 weight percent microcrystalline cellulose.

3. The particle of claim 1 which additionally contains a polymer coating over the pharmaceutical active ingredient.

4. The particle of claim 3 wherein the polymer coating is selected from the group consisting of methylaminoethylmethacrylate, methacrylic acid esters, cellulose acetate and polyvinylpyrrolidone.

5. A method for making a pharmaceutically active particle comprising:

providing a center core of greater than about 90 weight percent microcrystalline cellulose having an average particle size of about 160 to about 220 microns with a particle size standard deviation of from about 75 to about 200 and a tapped bulk density of from about 0.40 to about 0.45 grams per cubic centimeters;

coating said microcrystalline cellulose with a pharmaceutically active ingredient;

wherein the coated particle is from about 40 to about 75 weight percent microcrystalline cellulose; the pharmaceutically active ingredient is from about 25 to about 60 weight percent; has a particle size of from about 200 to about 325 microns; a particle size standard deviation of from about 30 to about 175 microns; wherein the coating of the microcrystalline cellulose is performed in the absence of a granulation step.

6. The method of claim 5 wherein the pharmaceutically active materials are deposited on the core via a solution layering process.

7. The method of claim 5 where a polymeric coating is applied over the pharmaceutically active material.

8. The method of claim 7 wherein the polymeric coating is selected from the group consisting of methylaminoethylmethacrylate, methacrylic acid esters and or cellulose acetate and polyvinylpyrrolidone.

9. The method of claim 8 wherein the coated particles and excipients are compressed to form tablets.

* * * * *